United States Patent [19]

Singh

[11] Patent Number: 5,290,960
[45] Date of Patent: Mar. 1, 1994

[54] DIACETYLENIC PHOSPHOLIPIDS CONTAINING HETEROATOM NEAR DIACETYLENIC FUNCTIONALITY FOR MODULATION OF MICROSTRUCTURE MORPHOLOGY

[75] Inventor: Alok Singh, Springfield, Va.

[73] Assignee: The United States of America as represented by the Secretary of the Navy, Washington, D.C.

[21] Appl. No.: 22,228

[22] Filed: Feb. 25, 1993

[51] Int. Cl.$^5$ ............................ C07F 7/00; C07F 9/00
[52] U.S. Cl. ........................................ 554/79; 554/80; 554/81; 556/404
[58] Field of Search ............................ 554/79, 80, 81; 556/404

[56] References Cited

U.S. PATENT DOCUMENTS

4,348,329 0/0000 Chapman ............................. 554/80
4,867,917 9/1989 Singh et al. ......................... 260/413

OTHER PUBLICATIONS

Singh et al., "A General Method for the Synthesis of Diacetylenic Acids", Printed in Synthetic Communications, 16(7)(1986), pp. 847–852.
Vaugh et al., J. Am. Chem. Soc'y 55, 3456 (1933).
Georger et al., "Helical and Tubular Microstructures Formed by Polymerizable Phosphatidylcholines", J. Am. Chem. Soc. 1987, 109, pp. 6169–6175.
Singh et al., "Self-Assembled Microstructures From a Polymerizable Ammonium Surfactant: Di(Hexacosa-12,14-Diynyl)Dimethylammonium Bromide", J. Chem. Soc. Chem. Commun., 1988, pp. 1222–1223.
Markowitz et al., "Self-Assembling Properties of 1,2-Diacyl-SN-Glycero-3-Phosphohydroxyethanol: A Headgroup-Modified Diacetylenic Phospholipid", Langmuir, vol. 7, No. 1, 1991, pp. 16–18.

*Primary Examiner*—Paul F. Shaver
*Assistant Examiner*—Joseph M. Conrad, III
*Attorney, Agent, or Firm*—Thomas E. McDonnell; John J. Karasek

[57] ABSTRACT

Novel diacetylenic phospholipids having the diacetylenic moieties chemically decoupled from the rest of the acyl chains by the inclusion of one or more heteroatom, preferably oxygen, spacers on the acyl chains have the chemical formula:

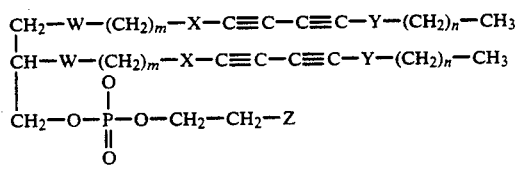

where m is 7, 8, 9, 10, 11, 12, or 13, where n is 8, 9, 10, 11, 12, or 13, where W is $-O(CO)-$ or $-OCH_2-$, where X is $-CH_2-$, $-OCH_2-$, $-SCH_2-$, $-NHCH_2-$, or $-SiMe_2CH_2-$, where Y is $-CH_2-$, $-CH_2O-$, $-CH_2S-$, $-CH_2NH-$, or $-CH_2SiMe_2-$, where Z is $-N(CH_3)_3$, saccharide, or $-ROH$ where R is $-(CH_2)_p-$ and p is 0, 1, 2 or 3, and where X and Y are not both $-CH_2-$. Novel tubules made from these diacetylenic phospholipids have high flexibility and variable morphology.

15 Claims, 2 Drawing Sheets

DIACETYLENIC PHOSPHOLIPIDS CONTAINING HETEROATOM NEAR DIACETYLENIC FUNCTIONALITY FOR MODULATION OF MICROSTRUCTURE MORPHOLOGY

BACKGROUND OF THE INVENTION

1. Field of the Invention

This invention relates to improvements in diacetylenic phospholipids and to lipid microstructures made from these lipids. More particularly, this invention relates to diacetylenic phospholipids with at least one heteroatom spacer on the diacetylenic chains, and to lipid microstructures made from these lipids.

2. Description of the Related Art

Diacetylenic phospholipids are used in making hollow microstructures, which may be spherical (vesicles) or cylindrical (tubules). These structures are useful for microencapsulation and for controlled release of drugs, antifouling agents in marine paints, and other substances. They offer an alternative to the polymers commonly used in these applications.

Problems with the available lipid microstructures include expensive reagents, microstructure morphology with fixed dimensions, and excessive rigidity.

Microstructure morphology with fixed dimensions puts restrictions on the size of a molecule to be encapsulated with an appropriate tubule. The known diacetylenic phospholipids self-assemble into tubules that have a diameter that is specific for a given phospholipid. This creates problems in encapsulating large-diameter molecules in tubules, since the known tubules cannot adapt their growth to the diameter of the molecule they are to encapsulate.

Excessively rigid tubules are prone to breakage during their formation and processing, and thus do not provide optimal controlled release of their contents.

SUMMARY OF THE INVENTION

Accordingly, it is an object of this invention to make inexpensive lipids suitable for making vesicles and tubules with high flexibility and microstructure morphology of variable diameter.

It is a further object of this invention to make lipid vesicles and tubules with high flexibility and microstructure morphology of variable diameter from these lipids.

These and additional objects of the invention are accomplished by the structures and processes hereinafter described.

The lipids of this invention have the chemical formula:

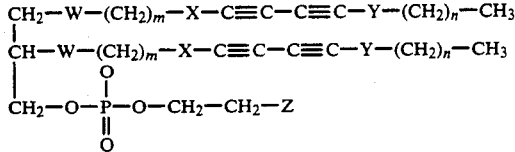

where m is 7, 8, 9, 10, 11, 12, or 13, where n is 8, 9, 10, 11, 12, or 13, where W is $-OCH_2-$ or $-O(CO)-$, where X is $-CH_2-$, $-OCH_2-$, $-SCH_2-$, $-NHCH_2-$, or $-SiMe_2CH_2-$, where Y is $-CH_2-$, $-CH_2O-$, $-CH_2S-$, $-CH_2NH-$, or $-CH_2SiMe_2-$, where Z is $-N(CH_3)_3$, saccharide, or $-ROH$ where R is $-(CH_2)_p-$ and p is 0, 1, 2, or 3, and where X and Y are not both $-CH_2-$.

The lipid microstructures of this invention are made by the process of:

a. dispersing the lipid of the invention in water at a temperature above the phase transition temperature, but below the temperature at which the dispersion boils;

b. cooling the dispersion to, and holding the dispersion at, a temperature above the freezing point of the dispersion, but not more than about 5° C.

The lipid microstructures of this invention are also made by the process of:

a. dissolving the lipid of the invention in a protic solvent miscible with water;

b. heating the lipid to a temperature above its phase transition temperature, up to the boiling point of the solution, and adding a quantity of water to the solution, to make a solution of water, protic solvent, and lipid, so that the ratio of protic solvent to water is at most about 9:1;

c. holding this solution at a temperature above the phase transition temperature, up to the boiling point of the solution, for at least about 1 hour, and allowing the lipid to cool to below the cooling phase transition temperature of the lipid.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DESCRIPTION OF THE PREFERRED EMBODIMENTS

As described above, the length of the diacetylenic chains can be varied. Preferably, m is 7. Preferably, n is at least 9. Lengthening the hydrocarbon chain to at least n=9 improves the flexibility and temperature stability of the tubules made from these lipids. Controlling the length of the diacetylenic chain provides a means for controlling the morphological features as well as the phase change temperature of the lipid.

As shown above, the lipid of the invention can have ester or ether linkages between the glycol backbone and the diacetylenic chains. Preferably, these linkages are ester linkages.

Inclusion of one or more heteroatom spacers in the acyl chains alters the local chemical environment of the diacetylenic groups, which in turn provides control of the lipid morphology. Selection of the heteroatom spacers preferably reflects the effect of the differing sizes, valences, and electronegativities of available heteroatom spacers on the local chemical environment of the diacetylenic groups. Most preferably, the heteroatom spacer is oxygen. Other preferred heteroatom spacers are sulphur, nitrogen, and silicon.

Selection of a headgroup preferably reflects any desired funtionality on the tubule surface. Most preferably, the headgroup (group Z above) is choline $(-N(CH_3)_3)$. Other preferred headgroups are alcohol $(-ROH)$ and saccharide. In the case where the headgroup is a saccharide, a preferred monosaccharide is galactose, and a preferred disaccharide is lactose. Saccaride headgroups are preferably coupled to the lipid backbone at the anomeric carbon of the saccharide (the carbon in the 1 position), due to the highly labile character of the hydroxyl group at this position.

Figure 1:
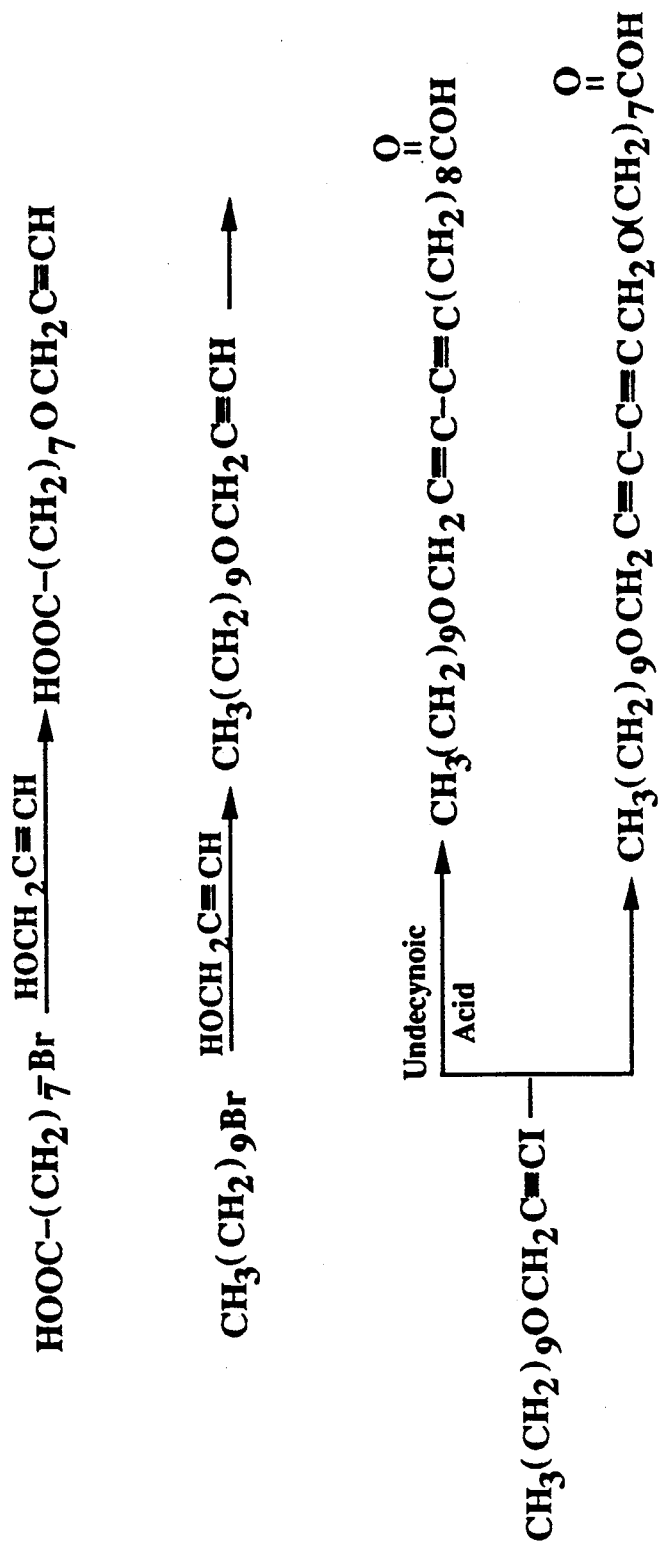
FIG. 1 shows a reaction scheme for producing lipid precursors for this invention.

As shown in FIG. 1, the preferred synthesis of diacetylenic acid with oxygen heteroatom spacers on both sides of the diacetylenic group, for attachment to the glycol backbone to synthesize the lipids of the invention, entails a series of reactions with inexpensive propargyl alcohol ($HOCH_2C\equiv CH$). A linear halocarboxylic acid (preferably the bromocarboxylic acid) is reacted with propargyl alcohol to form a linear carboxylic acid with an ether group and an n-alkyne group. A linear alkyl bromide is reacted with propargyl alcohol to form an n-alkyne with an ether group. This compound is n-iodinated, and the iodinated compound is reacted with the linear carboxylic acid with the ether group and the nalkyne group to form the diacetylenic acid with oxygen heteroatom spacers.

As further shown in FIG. 1, in the preferred synthesis of diacetylenic acid with a single oxygen heteroatom spacer, for attachment to glycol backbone to synthesize the lipids of the invention, a linear alkyl bromide is reacted with propargyl alcohol to form an n-alkyne with an ether group. This compound is n-iodinated, and the iodinated compound is reacted with a linear carboxylic acid with an n-alkyne group to form the diacetylenic acid with an oxygen heteroatom spacer.

Preferably, the diacetylenic acids are reacted with a complex of $CdCl_2$ and the appropriate glycol having the desired attached headgroup, to form the lipids of the invention.

Microstructures are formed from these lipids in both aqueous and mixed protic solvent/water systems. The preferred microstructure is formed in water preferably as follows: The lipid is dissolved in an organic solvent to make an essentially saturated solution. The solvent preferably is selected from the group $CHCl_3$, $CH_2Cl_2$, EtOEt, and EtOH. Most preferably, the solvent is $CHCl_3$.

The solvent is evaporated, leaving a layer of the lipid coating the interior of the container. Preferably, the solvent is evaporated under a stream of nonreactive gas, such as $N_2$ or Ar. Most preferably, the lipid is then kept under vacuum for at least an hour, to help ensure that all solvent is evaporated. Water is added to the container, preferably enough to make the ratio of lipid to water at least about 4 mg/ml, up to about 100 mg/ml, but preferably not more than 50 mg/ml.

The lipid is hydrated and then sonicated at a temperature above its phase transition temperature, up to the boiling point of the solution, to disperse the lipid in the water. Care should be taken to always keep the dispersion below its boiling point: boiling will result in microstructure rupture. Alternatively, after hydration the lipid is vortex-mixed between its phase transition temperature and its boiling point, to disperse the lipid in the water.

This lipid dispersion is then slowly cooled to a temperature between the freezing point of the dispersion and about 5° C. (preferably between about 3° C. and about 5° C., most preferably at about 4° C.) for most preferably about 3 hours. Care should be taken to always keep the dispersion above its freezing point: freezing will result in microstructure damage similar to frostbite in cells. In this context, slow cooling means slow cooling to about room temperature (i.e. allowing the lipid dispersion to cool to about room temperature), and cooling to a temperature between the freezing point of the dispersion and about 5° C. For tubule formation, the lipid preferably is then reheated to between its phase transition temperature and its boiling point, and allowed to cool gradually to below its crystallization temperature. Holding the lipid dispersion at this temperature for less than about 3 hours results in incomplete microstructure formation, holding the lipid dispersion at this temperature for more than about 3 hours confers no benefit.

The preferred microstructure formation in water/protic solvent is as follows: The lipid is dissolved in an protic solvent that is miscible with water, and heated to between its phase transition temperature and its boiling point.

Water is added to the solution, making a solution of water, protic solvent, and lipid, so that the ratio of protic solvent to water is preferably between about 9:1 and 0. Most preferably, the ratio of protic solvent to water is about 7:3. This ratio of water to protic solvent provides optimal tubule length and uniformity: too much water will result in tubules of mixed lengths, too much protic solvent will result in shorter tubules of mixed length.

This solution is held above the phase transition temperature for about 1 hour, and the lipid is allowed to cool to below its crystallization temperature, to form the microstructures. Most preferably, the protic solvent is ethanol. Other preferred protic solvents are methanol, propanol, and isopropanol.

Inclusion of two heteroatom spacers in the acyl chain results in the formation of vesicle microstructures. Inclusion of a single heteroatom spacer in the acyl chain results in the formation of both tubule and vesicle microstructures. A mixture of tubules and vesicles made from lipids with a single heteroatom spacer in the acyl chain can be converted to a mixture that is primarily composed of tubules with repetitions of the heating and cooling cycle of the microstructure formation; the fraction of tubule microstructures will increase as the heating and cooling cycle is repeated.

Having described the invention, the following examples are given to illustrate specific applications of the invention, including the best mode now known to perform the invention. These specific examples are not intended to limit the scope of the invention described in this application.

EXAMPLES

Example 1: Synthesis of 9-oxa-11-dodeoynoic acid $HOOC(CH_2)_7OCH_2C\equiv CH$

An ether solution of 8-bromooctanoic acid (15.1 g, 65 mmol) was reacted with 325 mmol propargyl alcohol dissolved in aqueous NaOH solution containing 975 mmol NaOH. After heating at 60° C. for 24 hours, the reaction was stopped by neutralizing the base with hydrochloric acid. Ether extraction provided 16 g of opaque white liquid, which was further purified by distillation under reduced pressure (160°–163° C./0.075 mm Hg). The sample was analyzed with $^1$H-NMR in $CDCl_3$, and the observed chemical shift peaks were at $\delta = 1.34$ (br singlet, 6H, —($\underline{CH_2}$)—), 1.61 (pentate center, 4H, —($\underline{CH_2}$)—), 2.35 (t, 2$\underline{H}$, $\underline{CH_2}$—COO), 2.42, (d, J=2.6 Hz, 1$\underline{H}$, C≡C$\underline{H}$), 3.51 (t, J=6.6 Hz, 2H, —$\underline{CH_2}$—O), and 4.14 (d, J=2.6 Hz, 2H, O—$\underline{CH_2}$—C≡$\overline{C}$). Observed IR (KBr) peaks were at 1709 ($\underline{C}$OOH), 2120 (—C≡C—) and 3298 (—C≡$\underline{CH}$) cm$^{-1}$.

Example 2: Synthesis of 4-oxatetradecyne CH₃(CH₂)₉OCH₂C≡CH

Propargyl alcohol (28.0 g, 0.5 mol) was mixed in NaOH solution (60 g in 90 ml H₂O and 100 ml ethanol). Bromododecane (114 g, 0.51 mol) was added to this solution and refluxed for 5 hours. The reaction mixture was then acidified and extracted with ether to recover 119 g of organic materials. Upon distillation (82°-84° C., 7.5 mm Hg) 16 g of 4-oxatetradecyne was obtained (17% yield). The sample was analyzed with ¹H-NMR in CDCl₃, and the observed chemical shift peaks were at $\delta = 0.88$ (t, 3H, —CH₃), 1.2-1.4 (br singlet, 14H, —CH₂—), 1.59 (pentate center, 2H, —CH₂—), 2.41 (d, $J = 2.2$ Hz, 1H, —C≡CH), 3.51 (t, $J = 6.6$ Hz, 2H, —CH₂—O), and 4.14 (d, $J = 2.2$ Hz, 2H, O—CH₂—C≡C). Observed IR (KBr) peaks were at 2120 (—C≡C—), and 3298 (—C≡CH) cm⁻¹.

Example 3: Synthesis of 1-iodo-4-oxa-tetradecyne CH₃(CH₂)₉OCH₂C≡CI

Following the procedure described in Vaughn, T. H., J. Am. Chemical Soc'y 55 3456 (1933), 4-oxatetradecyne (13 g, 66.2 mmol) was reacted with ethylmagnesium bromide (73 mmol) in dry ether. The resulting alkynyl magnesiumbromide was reacted with iodine and provided 15 g of 1-iodo-4-oxa-tetradecyne as viscous liquid (71% yield). The sample was analyzed with ¹H-NMR in CDCl₃, and the observed chemical shift peaks were at $\delta = 0.88$ (t, 3H, —CH₃), 1.23-1.4 (br singlet, 14H, —CH₂—), 1.57 (pentate center, 2H, —CH₂—), 3.51 (t, $J = 7.0$ Hz, 2H, —CH₂—O), and 4.28 (s, 2H, O—CH₂—C≡C). Observed IR (KBr) peak was at 2120 (—C≡C—) cm⁻¹; no peak was observed at 3298 (—C≡CH) cm⁻¹.

Example 4: Synthesis of 15-oxa-pentacosa-10,12-diynoic acid CH₃(CH₂)₉OCH₂C≡C—C≡CCH₂O(CH₂)₈COOH Undecynoic acid HOOC—(CH₂)₈C≡CH (7.15 g, 39.2 mmol) was coupled with 1-iodo-4-oxa-tetradecyne CH₃(CH₂)₉OCH₂C≡CI (13.9 g, 43 mmol) to yield 835 mg 15-oxa-pentacosa-10,12-diynoic acid (5% yield) after silica gel chromatography and recrystallization from hexane. The melting point for the product was 45° C. The sample was analyzed with ¹H-NMR in CDCl₃, and the observed chemical shift peaks were at $\delta = 0.88$ (t, 3H, —CH₃), 1.2-1.44 (br singlet, 22H, —CH₂—), 1.55 (m, 6H, —CH₂—), 2.27 (t, 2H, CH₂—COOH), 2.35 (t, 2H), CH₂—C≡C), 3.50 (t, $J = 6.8$ Hz, 2H, —CH₂—O), and 4.18 (s, 2H, O—CH₂—C≡C). Observed IR (KBr) peak was at 1704 cm⁻¹ (carbonyl); no peak was observed at 2120 (—C≡C—) cm⁻¹. The acid was converted to its anhydride with dicyclohexyl carbodiimide (DCC) in MeCl. Conversion to the anhydride was evidenced by the appearance of IR peaks at 1740 and 1810 cm⁻¹.

Example 5: Synthesis of 9,16-dioxa-hexacosa-11,13-diynoic acid CH₃(CH₂)₉OCH₂C≡C—C≡CCH₂O(CH₂)₇COOH Following the procedure described in Singh, A. & Schnur, J. M., Synthetic Comm. 16, 847 (1986), 1-iodo-4-oxa-tetradecyne (10 mmol) was coupled with 9-oxa-11-dodecynoic acid (1.98 g, 10 mmol) to produce 1.2 g 9,16-dioxa-hexacosa-11,13-diynoic acid (31% yield). The 9-oxa-11-dodecynoic acid was dissolved in aqueous KOH solution (1.1 mol eq.). CuCl (0.25 mol eq.) in ethylamine (70% aq. solution) was added, followed by 15 mg±5 mg hydroxyl amine hydrochloride NH₂OH.HCl crystals. To this solution (yellow) was then added, in small portions, the 1-iodo-4-oxa-tetradecyne dissolved in 10 ml of CH₃OH—CH₃CH₂OCH₂CH₃ (1:1). On addition of 1-iodo-4-oxa-tetradecyne the reaction mixture turned blue, and then yellow on addition of a few drops of 10% aqueous NH₂OH.HCl solution.

The reaction mixture was then acidified with 30% HCl and extrated with ether. The crude acid obtained from the ether extract was recrystallized from hexanes. The sample was analyzed with ¹H-NMR in CDCl₃, and the observed chemical shift peaks were at $\delta = 0.88$ (t, 3H, —CH₃), 1.2-1.44 (br singlet, 22H, —CH₂—), 1.55 (m, 4H, —CH₂—), 2.27 (t, 2H, CH₂—COOH), 2.35 (t, 2H, CH₂—C≡C), 3.50 (t, $J = 6.8$ Hz, 4H, —CH₂—O), and 4.18 (s, 4H, O—CH₂—C≡C). The product was converted to its anhydride by treating with DCC.

Example 6: Synthesis of Phospholipid where m=7, n=9, W=—O(CO)—, X=—OCH₂—, Y=—CH₂O—, and Z=—N(CH₃)₃

This phospholipid was prepared by reacting the anhydride of 9,16-dioxa-hexacosa-11,13-diynoic acid (1.15 g, 1.5 mmol) with glycerophosphorycholine-cadmium chloride complex (GPC.CdCl₂) (226 mg, 0.5 mmol) in the presence of dimethylaminopyridine (DMAP) (180 mg, 1.5 mmol), which is freshly distilled over phosphorous pentaoxide. The reaction vessel was degassed by purging argon in the reaction vessel, subjected to ultrasound bursts at room temperature for 10 minutes using a common laboratory ultrasound bath cleaner (45 KHz, 35 W), and stirred at room temperature for about 10 hours. The chloroform was then removed under reduced pressure (at 25° C.), and the residue was dissolved in 5 ml CH₂Cl₂—CH₃OH—H₂O 4:5:1 and passed through a column (1 cm×17 cm) of mixed-bed resin AG-501-X8 (D) (from Biorad Laboratories). The column was eluted with three column volume of the same solvent system. Solvent from resin-treated phospholipid solution was removed under vacuum. The vacuum-dried reaction mixture was then dissolved in a minimum volume of chloroform and the phospholipid was separated using a silica gel column (1 cm×20 cm). The column was first eluted with chloroform followed by a solution of CH₂Cl₂—CH₃OH—H₂O 65:25:4. The fractions containing pure phospholipids (checked by TLC) were combined. After this workup, 300 mg of pure product was obtained (60% yield). The sample was analyzed with ¹H-NMR in CDCl₃, and the observed chemical shift peaks were at $\delta = 0.88$ (t, 6H, —CH₃), 1.2-1.38 (br singlet, 40H, —CH₂—), 1.55-1.62 (m, 12H, —CH₂—), 2.30 (m, 4H, CH₂—COOH), 3.31 (s, 9H, —NMe₃), 3.49 (t, $J = 6.5$ Hz, 8H, —CH₂—O), 3.71-3.90 (m, 6H, —CH₂—O—CO, —CH₂—N), 4.18 (s, 8H, O—CH₂—C≡C), 4.2-4.4 (m, 2H, 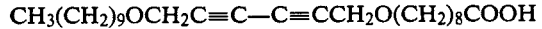—P—O—CH₁—), 5.19 (s, 1H, —CHO—).

Example 7: Synthesis of Phospholipid where m=7, n=9, W=—O(CO)—, X=—CH₂—, Y=—CH₂O—, and Z=—N(CH₃)₃

The phospholipid was prepared by reacting the anhydride of 15-oxa-pentacosa-10,12-diynoic acid (696 mg, 0.97 mmol), with GPC.CdCl₂ (137 mg, 0.31 mmol) in the presence of DMAP (119 mg, 0.97 mmol), which is freshly distilled over phosphorous pentaoxide. The reaction vessel was degassed by purging argon in the reaction vessel, subjected to ultrasound bursts at room temperature for 10 minutes using a common laboratory ultrasound bath cleaner (45 KHz, 35 W), and stirred at room temperature for about 10 hours. The chloroform was then removed under reduced pressure (at 25° C.), and the residue was dissolved in 5 ml $CH_2Cl_2$—$CH_3OH$—$H_2O$ 4:5:1 and passed through a column (1 cm×17 cm) of mixed-bed resin AG-501-X8 (D) (from Biorad Laboratories). The column was eluted with three column volume of the same solvent system. Solvent from resin-treated phospholipid solution was removed under vacuum. The vacuum-dried reaction mixture was then dissolved in a minimum volume of chloroform and the phospholipid was separated using a silica gel column (1 cm×20 cm). The column was first eluted with chloroform followed by a solution of $CH_2Cl_2$—$CH_3OH$—$H_2O$ 65:25:4. The fractions containing pure phospholipids (checked by TLC) were combined. After this workup, 153 mg of pure product was obtained (51% yield). The sample was analyzed with $^1$H-NMR in $CDCl_3$, and the observed chemical shift peaks were at $\delta$=0.88 (t, 6H, —$CH_3$), 1.2-1.75 (br singlet, 56H, —$CH_2$—), 2.23-2.44 (m, 8H, $CH_2$—COOH), 3.36 (s, 9$\overline{H}$, —$NMe_3$), 3.49 (t, J=6.5 Hz, 4H, —$CH_2$—O), 3.71-4.12 (m, $\overline{6H}$, —$CH_2$—O—CO, —$CH_2$—$\overline{N}$), 4.18 (s, 4H, O—$CH_2$—C≡C), 4.2-4.42 (m, 2H, —P—O—$CH_2$), 5.23 (s, 1$\overline{H}$, —CHO—).

Figure 2:
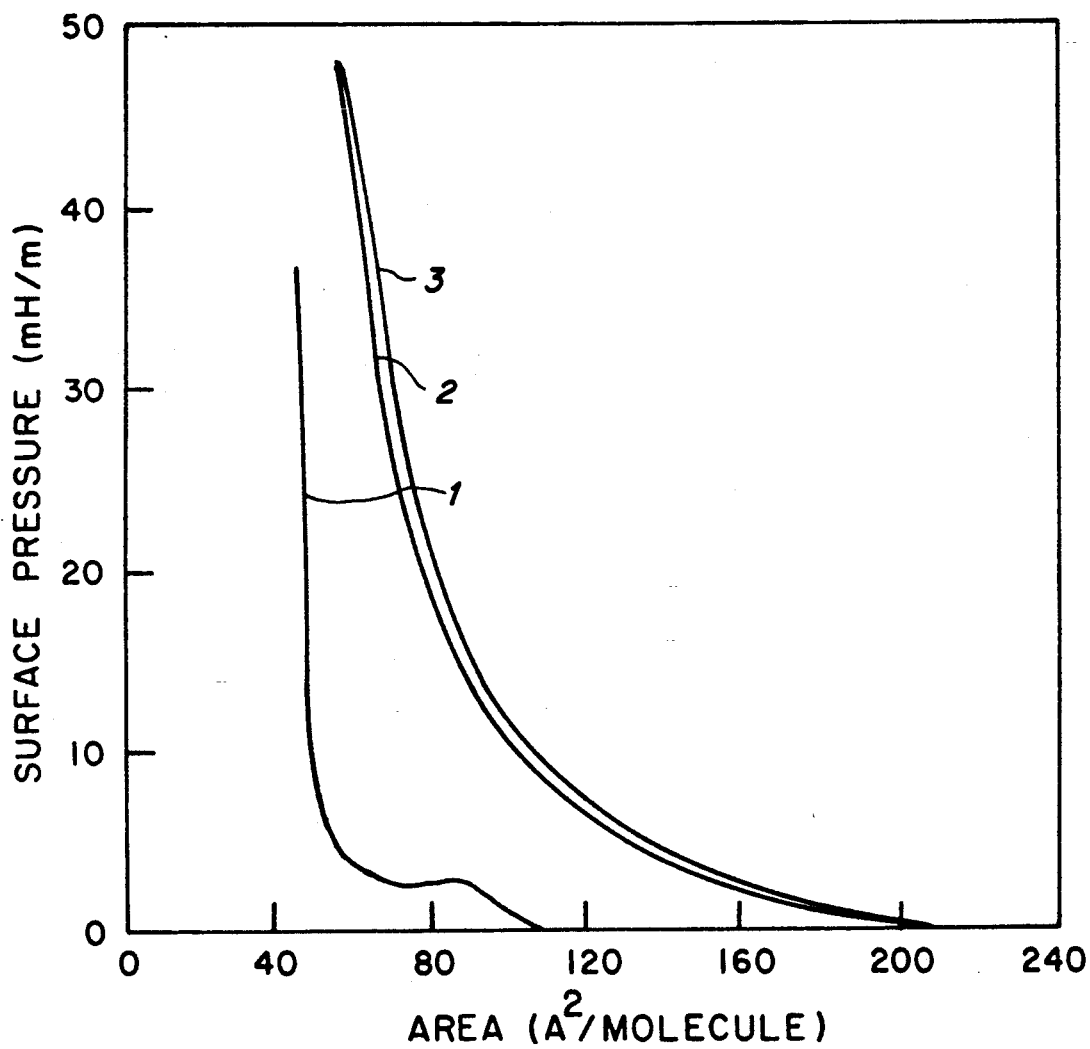
FIG. 2 compares the force area isotherms of lipids with and without heteroatom spacers.

The Langmuir force area isotherms (23° C.) of the lipids made in Examples 6 (curve 2) and 7 (curve 3) are shown in FIG. 2, along with the force area isotherm of the analogous lipid without the heteroatom spacers (curve 1). The higher area per molecule of the lipids made in Examples 6 and 7 is indicative of the disordering effect the heteroatom spacers have on the packing of these lipids. While not wishing to be bound by theory, applicants hypothesize that the flexibility of the tubules made from these lipids, as well as the ability of these tubules to grow to varying diameters, is related to the disordering effect the heteroatom spacers have on the lipids.

Example 8: Preparation of Lipid Microstructure from Phospholipid where m=7, n=9, W=—O(CO)—, X=—$OCH_2$—, Y=—$CH_2O$—, and Z=—$N(CH_3)_3$ The lipid was dissolved in the minimum amount of $CHCl_3$ (2 mg lipid, between 0.2 ml and 0.4 ml solvent). The solvent was evaporated under a stream of Ar, leaving a thin layer of the lipid coating the bottom of the test tube. The lipid was then kept under vacuum for one hour. The lipid was then hydrated and vortex mixed in water (2 mg/ml) above the $T_m$ of the lipid. The lipid dispersion was allowed to cool to room temperature (1° C./min).

Example 9: Alternative Preparation of Lipid Microstructure from Phospholipid where m=7, n=9, W=—O(CO)—, X=—$OCH_2$—, Y=—$CH_2O$—, and Z=—$N(CH_3)_3$ The lipid was dissolved in the minimum amount of $CHCl_3$ (2 mg lipid, between 0.2 ml and 0.4 ml solvent). The solvent was evaporated under a stream of Ar, leaving a thin layer of the lipid coating the bottom of the test tube. The lipid was then kept under vacuum for one hour. The lipid was then hydrated and sonicated in water (2 mg/ml) above the $T_m$ of the lipid. The lipid dispersion was allowed to cool to room temperature (1° C./min) and then kept at 4° C. for 3 hours. The lipid was then reheated above the phase transition tempeature and again allowed to cool to room temperature (1° C./min).

Example 10: Preparation of Lipid Microstructure from Phospholipid where m=7, n=9, W=—O(CO)—, X=—$CH_2$—, Y=—$CH_2O$—, and Z=—$N(CH_3)_3$ The lipid microstructure was prepared as in Example 8. Lipid tubules grown in Examples 8, 9, and 10 were observed (by optical microscopy and TEM) to be flexible and to vary in diameter from about 0.4 μm to about 5 μm.

Obviously, many modifications and variations of the present invention are possible in light of the above teachings. It is therefore to be understood that, within the scope of the appended claims, the invention may be practiced otherwise than as specifically described.

What is claimed is:

1. A lipid with the chemical formula

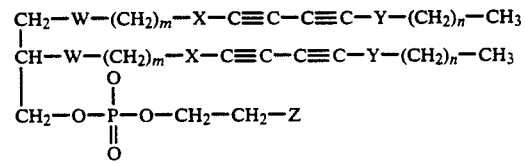

wherein m is 7, 8, 9, 10, 11, 12, or 13, wherein n is 8, 9, 10, 11, 12, or 13, wherein W is —O(CO)— or —$OCH_2$—, wherein X is —$CH_2$—, —$OCH_2$—, —$SCH_2$—, —$NHCH_2$—, or —$SiMe_2CH_2$—, wherein Y is —$CH_2$—, —$CH_2O$—, —$CH_2S$—, —$CH_2NH$—, or —$CH_2SiMe_2$—, wherein Z is —$N(CH_3)_3$, saccharide, or —ROH wherein R is —$(CH_2)_p$— and p is 0, 1, 2 or 3, and wherein X and Y are not both —$CH_2$—.

2. The lipid of claim 1, wherein m is 7, n is 9, W is —O(CO)—, X is —$OCH_2$—, Y is —$CH_2O$—, and Z is —$N(CH_3)_3$.

3. The lipid of claim 1, wherein m is 7, n is 9, W is —O(CO)—, X is —$CH_2$—, Y is —$CH_2O$—, and Z is —$N(CH_3)_3$.

4. The lipid of claim 1, wherein Z is galactose or lactose linked to the lipid backbone through an ether bond at the anomeric carbon of said saccharide.

5. A composition of lipid tubules, made by the process of: providing, in a vessel, a lipid with the chemical formula

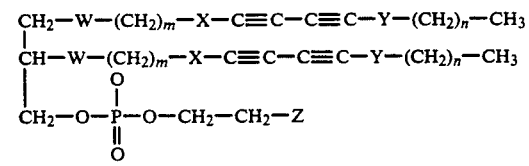

wherein m is 7, 8, 9, 10, 11, 12, or 13, wherein n is 8, 9, 10, 11, 12, or 13, wherein W is —O(CO)— or —$OCH_2$—, wherein X is —$CH_2$—, —$OCH_2$—, —$SCH_2$—, —$NHCH_2$—, or —$SiMe_2CH_2$—, wherein Y is —$CH_2$—, —$CH_2O$—, —$CH_2S$—, —$CH_2NH$—, or —$CH_2SiMe_2$—, wherein Z is —$N(CH_3)_3$, saccharide, or —ROH wherein R is —$(CH_2)_p$— and p is 0, 1, 2 or 3, and wherein X and Y are not both —$CH_2$—, and also providing water in said vessel to hydrate said lipid;

dispersing said lipid in said water at a temperature above the phase transition temperature of the lipid;

cooling said lipid dispersion to a temperature between the freezing temperature of said dispersion and about 5° C.

6. The composition of claim 5, further comprising the step of reheating said lipid to above said phase transition temperature of said lipid, and allowing said lipid to cool to below the crystallization temperature of said lipid, after said step of cooling said lipid dispersion to about room temperature, then cooling and holding said dispersion at a temperature between the freezing temperature of said dispersion and about 5° C.

7. The composition of claim 5, wherein said step of providing, in a vessel, said lipid and said water further comprises the steps of:

providing, in a vessel, said lipid;

forming an essentially saturated solution of said lipid by adding a solvent for said lipid to said vessel;

evaporating said solvent from said vessel, whereby said vessel is coated with a film of said lipid;

adding water to said vessel, wherein the ratio of said lipid to said water is at least about 4 mg/ml;

8. The composition of claim 7 wherein said solvent for said lipid is $CHCl_3$, $CH_3Cl$, EtOEt, or ethanol.

9. The composition of claim 5, wherein said step of dispersing said lipid in said water comprises sonicating said lipid at a temperature between the phase transition temperature for said lipid and the boiling point of said dispersion.

10. The composition of claim 5, wherein said step of cooling and holding said dispersion at a temperature between the freezing point of said dispersion and about 5° C. comprises cooling and holding said dispersion at a temperature of about 4° C. for at least about 3 hours.

11. A composition of lipid tubules, made by the process of: providing, in a vessel, a lipid with the chemical formula

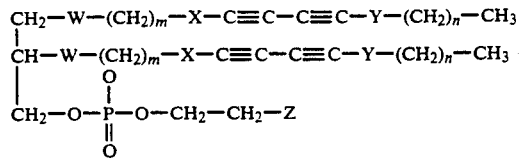

wherein m is 7, 8, 9, 10, 11, 12, or 13, wherein n is 8, 9, 10, 11, 12, or 13, wherein W is —O(CO)— or —$OCH_2$—, wherein X is —$CH_2$—, —$OCH_2$—, —$SCH_2$—, —$NHCH_2$—, or —$SiMe_2CH_2$—, wherein Y is —$CH_2$—, —$CH_2O$—, —$CH_2S$—, —$CH_2NH$—, or —$CH_2SiMe_2$—, wherein Z is —$N(CH_3)_3$, saccharide, or —ROH wherein R is —$(CH_2)_p$— and p is 0, 1, 2 or 3, and wherein X and Y are not both —$CH_2$— of claim 1;

dissolving said lipid by adding a protic solvent miscible with water to said vessel to make a solution of said lipid and said protic solvent;

heating said lipid to a temperature between the phase transition temperature for said lipid and the boiling point of said solution, and adding water to said vessel to make a solution of said water, said protic solvent and said lipid, so that the ratio of protic solvent to water in said vessel is between about 0 and about 9:1;

holding said solution above said phase transition temperature for at least about 1 hour, and allowing said lipid to cool to below the crystallization temperature of said lipid.

12. The composition of lipid tubules of claim 11, wherein m is 7, n is 9, W is —O(CO)—, X is —$OCH_2$—, Y is —$CH_2O$—, and Z is —$N(CH_3)_3$.

13. The composition of lipid tubules of claim 11, wherein m is 7, n is 9, W is —O(CO)—, X is —$CH_2$—, Y is —$CH_2O$—, and Z is —$N(CH_3)_3$.

14. The composition of lipid tubules of claim 11, wherein said protic solvent is ethanol, methanol, propanol, or isopropanol.

15. The composition of lipid tubules of claim 11, wherein said ratio of protic solvent to water in said vessel is about 7:3.

* * * * *